US009199406B2

(12) United States Patent
Winzinger et al.

(10) Patent No.: US 9,199,406 B2
(45) Date of Patent: Dec. 1, 2015

(54) APPARATUS FOR THE SHAPING OF PLASTICS MATERIAL PRE-FORMS WITH A CLEAN ROOM

(71) Applicant: KRONES AG, Neutraubling (DE)

(72) Inventors: Frank Winzinger, Regensburg (DE); Florian Geltinger, Donaustauf (DE)

(73) Assignee: KRONES, AG, Neutraubling (DE)

( * ) Notice: Subject to any disclaimer, the term of this patent is extended or adjusted under 35 U.S.C. 154(b) by 0 days.

(21) Appl. No.: 14/474,348

(22) Filed: Sep. 2, 2014

(65) Prior Publication Data
US 2015/0072036 A1    Mar. 12, 2015

(30) Foreign Application Priority Data
Sep. 12, 2013 (DE) .............. 20 2013 008 055 U

(51) Int. Cl.
B29C 49/46 (2006.01)
B29C 49/42 (2006.01)
B65B 55/08 (2006.01)
B65B 55/10 (2006.01)
A61L 2/08 (2006.01)
A61L 2/20 (2006.01)
B29C 49/28 (2006.01)
(Continued)

(52) U.S. Cl.
CPC . *B29C 49/46* (2013.01); *A61L 2/08* (2013.01); *A61L 2/208* (2013.01); *B29C 49/28* (2013.01); *B29C 49/4205* (2013.01); *B29C 49/4252* (2013.01); *A61L 2202/12* (2013.01); *A61L 2202/122* (2013.01); *A61L 2202/23* (2013.01); *B29C 49/06* (2013.01); *B29C 49/36* (2013.01); *B29C 2049/4697* (2013.01); *B29C 2049/4892* (2013.01); *B65B 55/08* (2013.01); *B65B 55/10* (2013.01)

(58) Field of Classification Search
CPC ............ B29C 49/46; B29C 2049/4892; B29C 2049/4697; B29C 49/4205; B29C 49/4252; B29C 2049/4673; B65B 55/08; B65B 55/10; A61L 2202/123; A61L 2202/122; A61L 2202/12; A61L 2/08; A61L 2/208
See application file for complete search history.

(56) References Cited

U.S. PATENT DOCUMENTS 8,696,339 B2    4/2014 Geltinger et al.
8,708,680 B2    4/2014 Geltinger et al.
(Continued)

FOREIGN PATENT DOCUMENTS

CN    102773998    11/2012
EP    2388127    11/2011
(Continued)

OTHER PUBLICATIONS

European Search Report dated Feb. 2, 2015 issued in corrpesonding European application 14184626.1-1706.

*Primary Examiner* — Robert B Davis
(74) *Attorney, Agent, or Firm* — Onello & Mello, LLP

(57) ABSTRACT

An apparatus comprises a conveying device and a plurality of blow molding stations arranged on the conveying device. Each blow molding station includes a blow mold. A clean room is provided inside which the plastics material pre-forms are conveyed. The blow mold has two lateral parts and a bottom part that jointly form a cavity inside which a plastics material pre-form is shaped into a plastics material container. A drive device moves the lateral parts or the bottom part of the blow mold. A coupling device couples the drive device to a lateral part. A mounting device mounts the coupling device.

20 Claims, 5 Drawing Sheets

(51) Int. Cl.
*B29C 49/06* (2006.01)
*B29C 49/36* (2006.01)
*B29C 49/48* (2006.01)

(56) References Cited

U.S. PATENT DOCUMENTS

| | | |
|---|---|---|
| 8,944,794 B2 | 2/2015 | Geltinger et al. |
| 2011/0287126 A1 | 11/2011 | Geltinger et al. |
| 2012/0225156 A1 | 9/2012 | Geltinger et al. |
| 2012/0248659 A1 | 10/2012 | Neubauer et al. |
| 2012/0261865 A1 | 10/2012 | Neubauer et al. |
| 2012/0286459 A1 | 11/2012 | Neubauer et al. |
| 2013/0064920 A1 | 3/2013 | Geltinger et al. |
| 2014/0103584 A1 | 4/2014 | Pagliarini et al. |

FOREIGN PATENT DOCUMENTS

| | | |
|---|---|---|
| EP | 2495089 | 9/2012 |
| EP | 2495090 | 9/2012 |
| EP | 2511070 | 10/2012 |
| EP | 2570251 | 3/2013 |
| WO | 2012153268 | 11/2012 |

APPARATUS FOR THE SHAPING OF PLASTICS MATERIAL PRE-FORMS WITH A CLEAN ROOM

CROSS-REFERENCE TO RELATED APPLICATIONS

A claim for priority under 35 U.S.C. §119 is made to German Patent Application No. 20 2013 008 055.8 filed Sep. 12, 2013, in at the German Intellectual Property Office, the entire contents of which are hereby incorporated by reference.

BACKGROUND

The present inventive concepts relate to an apparatus for the shaping of plastics material containers.

In the drinks-producing industry, plastics material containers are widely used. Plastics material containers are typically produced from plastics material pre-forms according to a shaping procedure, and in particular a blow moulding procedure. In this case, it is typical for blow moulding wheels to be provided on which a plurality of blow moulding stations are arranged. The plastics material pre-forms are expanded against an inner wall of the corresponding blow mould by being acted upon with compressed air inside these blow moulding stations. Blow moulding wheels of this type are preferably designed in the form of a rotor and revolve in a continuous manner about their axes of rotation. An axis of rotation is, in particular, orientated vertically. A lengthening of the axis of rotation thus intersects a center point of Earth.

For many beverages, it is necessary in this case to fill them under aseptic conditions. In this case, it is known for a sterilization process for the aseptic filling to start with the sterilization of finished bottles in a clean room. All the processes which have been carried out previously in the prior art, such as the production of the pre-forms, the conveying thereof, the heating thereof, and the blow moulding thereof to form the bottle, take place in a non-sterile environment. It is necessary to sterilize a relatively large area, namely, the area of the already finished plastic bottle.

The sterilization of containers which are intended to be filled with sensitive filling products can be carried out, for example, by the filling products being heated and filled in a hot state, and by the inside of the bottle being disinfected jointly with the hot filling products. In addition, it is also possible for the empty container to be disinfected separately before the filling procedure and to be filled under aseptic conditions with filling products sterilized at another location. The sterility of the empty container is achieved in this case by chemical disinfection agents such as peracetic acid (wet) or hydrogen peroxide (dry). To this end, the containers are moved into a so-called isolator in which they are acted upon with the disinfection agent which has to act for a specified time and then has to be removed again with a considerable outlay. In this case, a problem with respect to a residual quantity arises. The aseptically encapsulated filling means is arranged directly adjoining this isolator. This technology, however, is still relatively expensive.

SUMMARY

An object of the present inventive concepts is to optimize the mounting of a coupling device and at the same time to reduce the outlay for sterilizing or keeping sterile a shaping unit or blow moulding device respectively for containers in this case. Advantageous embodiments and further developments form the subject matter of the sub-claims.

In one aspect, an apparatus that forms plastics material containers from pre-forms, comprises a conveying device; a plurality of blow moulding stations arranged on the conveying device, wherein each of the blow moulding stations includes a blow mould. The blow mould has two lateral parts and a bottom part, The lateral parts and the bottom part jointly form a cavity inside which a plastics material pre-form is shaped into a plastics material container. At least the areas of the lateral parts bounding the cavity and of the bottom part are inside a clean room. The apparatus further comprises at least one first drive device that moves the lateral parts or the bottom part of the blow mould, wherein the first drive device is situated at least in part outside the clean room; a sealing device that seals the clean room from a region at which the drive device is situated; a coupling device that couples the at least one drive device to at least one lateral part of the two lateral parts, wherein the coupling device extends through at least one wall bounding the clean room; and a mounting device that mounts the coupling device, wherein the mounting device is fastened to the wall and extends from the fastening only to one side of the wall.

In some embodiments, the mounting device has a first portion that abuts the wall and a second portion that is at a right angle to the wall.

In some embodiments, the mounting device is fixedly and immovably connected to the wall.

In some embodiments, the mounting device comprises two mounting devices for mounting the coupling device, wherein the two mounting devices extend from the wall in a direction of the clean room or in a direction of the environment.

In some embodiments, the first mounting device extends from the wall in the direction of the clean room and the second mounting device extends in the direction of the environment.

In some embodiments, the first mounting device is screwed to the wall and the second mounting device is welded to the wall.

In some embodiments, the first and the second mounting devices are constructed and arranged to mount a common coupling device.

In some embodiments, one face of the mounting device is formed at an angle to a horizontal axis. In some embodiments, the angle ranges from 5° to 85°. In some embodiments, the angle ranges from 10° to 30°.

In some embodiments, the mounting device extends from the wall in a direction of the clean room, and wherein the apparatus further comprises a support device at a region external the wall.

In some embodiments, the support device is adapted to a recess in the wall in order to insert or replace at least one blow moulding station of the blow moulding station.

In some embodiments, the sealing device is between the coupling device and the mounting device.

In some embodiments, the coupling device actuates a stressing device, the bottom part of the blow mould, or a locking device.

In some embodiments, the mounting device is at a horizontal distance of up to 10 cm from the blow mould.

In some embodiments, the mounting device is at a horizontal distance of up to 5 cm from the blow mould.

In some embodiments, the mounting device is at a horizontal distance of up to 3 cm from the blow mould.

In some embodiments, the mounting device is positioned at least in part at a level of the blow mould in the direction of an x-axis.

In another aspect, provided is a plant that produces plastics material containers, comprising: a clean room and an apparatus. The apparatus comprises a conveying device that conveys pre-forms from which the plastics material containers are produced; a plurality of blow moulding stations arranged on the conveying device, wherein each of the blow moulding stations includes a blow mould, wherein the blow mould has two lateral parts and a bottom part, wherein the lateral parts and the bottom part jointly form a cavity inside which a plastics material pre-form is shaped into a plastics material container; at least one first drive device that moves the lateral parts or the bottom part of the blow mould; a coupling device that couples the at least one first drive device to at least one lateral part of the two lateral parts; and a mounting device that mounts the coupling device, wherein the mounting device is fastened to the wall and extends from the fastening only to one side of the wall. The plant further comprises a heating device arranged on the conveying device of the preforms, the heating device upstream from the conveying apparatus.

In some embodiments, the plant further comprises a sterilization device which sterilizes at least one area of the plastics material pre-forms before reaching the apparatus.

In some embodiments, the plant further comprises a clean room which is arranged upstream of the apparatus in the conveying direction of the plastics material preforms.

BRIEF DESCRIPTION OF THE FIGURES

The above and other objects and features will become apparent from the following description with reference to the following figures, wherein like reference numerals refer to like parts throughout the various figures unless otherwise specified. In the drawings.

DETAILED DESCRIPTION

Figure 1:
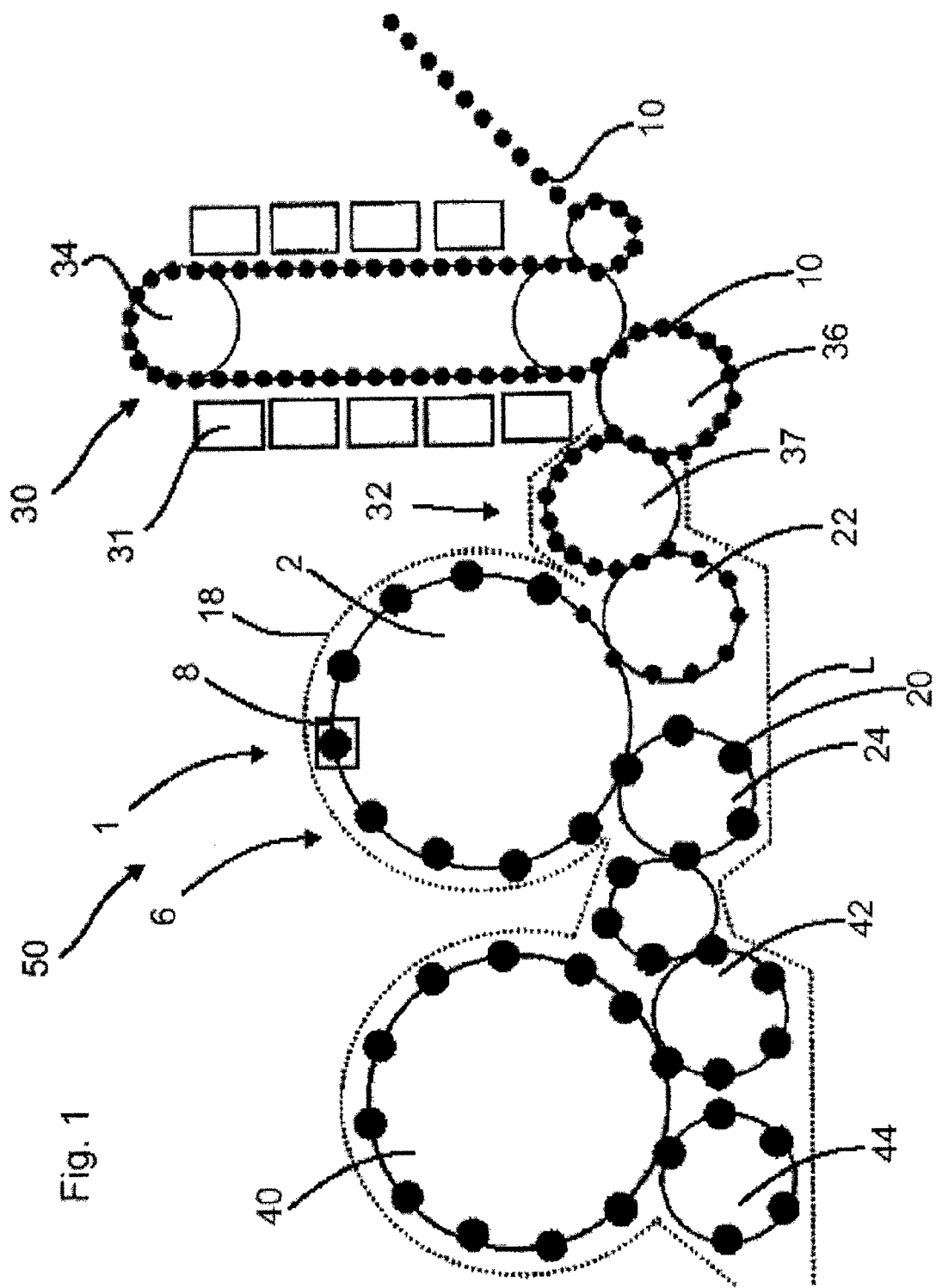
FIG. 1 is a diagrammatic illustration of a conventional plant for producing plastics material containers.

Advantages and features of the present inventive concepts and methods of accomplishing the same may be understood more readily by reference to the following detailed description of preferred embodiments and the accompanying drawings. The present inventive concepts may, however, be embodied in many different forms and should not be construed as being limited to the embodiments set forth herein. Rather, these embodiments are provided so that this disclosure will be thorough and complete and will fully convey the concept of the inventive concepts to those skilled in the art, and the present inventive concepts will only be defined by the appended claims. In the drawings, the thickness of layers and regions are exaggerated for clarity.

It will be understood that when an element or layer is referred to as being "on" or "connected to" another element or layer, it can be directly on or connected to the other element or layer or intervening elements or layers may be present. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The use of the terms "a" and "an" and "the" and similar referents in the context of describing the inventive concepts (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present inventive concepts.

It is usually desirable, not for the plastic bottle itself, but for the plastics material pre-form, to be sterilized, since the latter has a considerably smaller surface. Nevertheless, it is necessary for the containers to be conveyed under sterile conditions, in particular in a continuous manner, after the sterilization thereof, at least until they are closed, in order to prevent further contamination of the containers in this way.

EP 2 388 129 A1, incorporated by reference herein in its entirety, refers to an apparatus for shaping plastics material pre-forms into plastics material containers with a clean room in which are arranged the blow moulds, i.e., the lateral parts and the bottom part. The drive devices for moving the lateral parts and the bottom part respectively are, however, arranged at least in part outside the clean room. In addition, coupling devices for coupling the drive devices to the lateral parts and the bottom part respectively are present, which pass through the boundary of the clean room. The coupling devices are enclosed in folding bellows which permit a translational or rotational movement of the coupling device, while at the same time the clean room can be kept sterile.

A drawback with the use of folding bellows is that folding bellows are very expensive as sealing means and, in addition, it is very difficult to clean or sterilize respectively the harmonica-like interspaces of the folding bellows.

Pivot axles which are fixedly and immovably connected to the upper and the lower wall are present in order to mount the mould carrier halves. A seal, for example, an O ring, is provided at the point at which the pivot axle passes through the clean room boundary. The pivoting movement of the mould carrier halves about the pivot axles is initiated in this case by arms which are attached horizontally and which constitute a coupling device and are sealed off by folding bellows.

In addition, EP 2 495 086 A1, incorporated by reference herein in its entirety, displays pivot shafts which serve to unfold the blow mould carriers. In contrast to EP 2 388 129 A1 incorporated by reference above, the pivot shafts are attached in a rotatable manner to the upper and lower walls and no additional arms are required for the pivoting. A mounting of these shafts can be situated outside the clean room. Details concerning the mounting are not described. However, since the pivot shafts are coupled in each case to drive devices, it is well-known that the pivot shafts are mounted in the region of the drive devices and are sealed off at the boundary of the clean room by the folding bellows described above.

A problem with a mounting of this type is that moments which heavily load the coupling device are caused by the movement of the lateral parts on the pivot shaft and, in addition, it is difficult to clean or sterilize the folding bellows.

Features of the present inventive concepts address the foregoing by optimizing the mounting of a coupling device and at the same time to reduce the outlay for sterilizing or keeping sterile a shaping unit or blow moulding device respectively for containers in this case. An apparatus according to embodiments of the present inventive concepts relates to the shaping of plastics material pre-forms into plastics material containers, and has a conveying device on which are arranged a plurality of blow moulding stations. Each blow moulding station has a blow mould. The apparatus has or can be part of a clean room inside which the plastics material pre-forms can be conveyed. In addition, each blow mould has two lateral parts and a bottom part. The lateral parts and the bottom part jointly form a cavity inside which a plastics material pre-form is capable of being shaped into a plastics material container. At least the areas of the lateral parts bounding this cavity and of the bottom part are always situated inside the clean room. In addition, at least one drive device is provided for moving the lateral parts or at least for moving the bottom part.

At least one of the drive devices or the drive direction, respectively, is situated at least in part outside the clean room. A sealing device is provided, which seals off the clean room from a region in which the drive device is situated. In addition, at least one of the drive devices situated outside the clean room is coupled to a lateral part by way of a coupling device. This coupling device extends through at least one wall bounding the clean room.

According to embodiments of the present inventive concepts, a mounting device may be provided for mounting the coupling device, which is fastened to the wall and which extends from the fastening only to one side of the wall.

The apparatus according to embodiments of the present inventive concepts has an advantage that a folding bellows is not necessary for sealing purposes, but instead includes a circular seal in the form of a ring. In this way, the apparatus can be cleaned or sterilized considerably better than a conventional apparatus.

The words "extends only to one side of the wall" should be understood to mean that one end of the mounting device is fastened to the wall and the other end faces either in the direction of the clean room or in the direction of the environment. The mounting device does not extend, however, through the wall in both directions. The first end always rests against an external region, an internal region, or a lateral region of the wall, and can extend beyond the region of the wall only in one direction.

The internal region of the wall is the surface of the wall which faces the clean room and which is situated in the vicinity of the through hole of the coupling device. The external region is the surface of the wall which faces away from the clean room or faces the environment respectively and which is situated in the vicinity of the through hole of the coupling device. The lateral region is the surface of the inner side of the through hole of a coupling device through the wall which extends parallel to the axis of the coupling device.

A mounting device which extends from the wall into the clean room has the advantage that the mounting device is situated as close as possible to the point at which the force resulting from the movement of the lateral parts acts upon the coupling device and, as a result, this force can be better intercepted so as to deform (precision) or load (fatigue strength), respectively, the coupling device to the smallest possible degree.

If the mounting device extends, however, from the wall in the direction of the environment, this has the advantage that fewer faces—on which germs or related undesirable entities can settle or which have to be sterilized respectively—are present inside the clean room. In addition, the clean room can be designed in a more compact manner, i.e., smaller as a whole.

It is preferable for the mounting device to start completely at the level of the wall and to be attached substantially at a right angle to the wall. In this case the mounting device can be in the form of a tube or other hollow cylinder.

The phrase "starting completely at the level of the wall" is to be understood to mean that one end of the mounting device is fastened, preferably welded or screwed, to the lateral, inner or external region of the wall. In this case "completely" means that the first end of the mounting device—if the other end projects into the clean room—extends at most to the plane of the external region of the wall, but does not go beyond it. The first end can consequently be fastened to the lateral region and/or to the internal region, but not to the external region. The same applies in a similar manner to a mounting device which extends in the direction of the environment. This terminates, however, in the plane of the internal region and is attached to the lateral region and/or to the external region.

In an embodiment, two mounting devices for mounting the coupling device are present, the two mounting devices extending from the wall in the direction of the clean room or in the direction of the environment. In particular, the two mounting devices are attached to different walls, for example, one mounting device is coupled to to an upper wall and the other mounting device is coupled to a lower wall of the clean room.

Mounting devices which extend in the direction of the clean room have the advantage that the mounting devices can engage as close as possible to the point at which a force acts upon the coupling device as a result of the movement of the lateral parts, and so the coupling devices are loaded to a reduced degree. In addition, it is advantageous, if the blow moulding station as a whole plus part of the lower wall is replaced, for the module of the blow moulding station to be set down on a flat carrier, in particular, close to the bottom, or directly on the bottom, since the wall constitutes a flat face from below.

If the mounting devices extend in the direction of the environment, this has the advantage that fewer faces which have to be sterilized and on which germs or the like can settle are arranged in the clean room and, in this way, the clean room is easier to sterilize. A further advantage is that the annular clean room can be as compact as possible.

It is advantageous for two mounting devices for mounting the coupling device to be present: the first mounting device extending from the wall in the direction of the clean room and the second mounting device extending in the direction of the environment. Consideration is also given to arranging the lower mounting device in the clean room and the upper one outside.

It is preferable for the mounting device to be connected to the wall in an immovable manner. The mounting device can be connected to the wall in an immovable manner during operation. In this case, the mounting device can be either welded or screwed or clamped to the wall. If the mounting device is screwed to the wall, it can be adjusted when the machine is at a stop. In particular, the mounting device has, in addition, one or more mounting means which allow a rotational movement of the coupling device. In addition, a sealing device is arranged between the clean room and the mounting means. This sealing device can be attached to the mounting device, namely, in such a way that it touches the coupling device and the mounting device. Alternatively, for sealing purposes, it is also possible for the mounting device as a whole to be arranged inside a folding bellows which is fastened to the wall on one side and to the coupling device on the other side. In this case, no further sealing device is necessary between the mounting device and the coupling device, since the mounting device as a whole does not come into contact with the clean room. The first variant for sealing, however, is more advisable in terms of the capacity for cleaning or sterilization, since the mounting device preferably has a smooth surface and can therefore be sterilized considerably better than a harmonica-like folding bellows.

It is advantageous for a first mounting device to be screwed to the wall and for a second mounting device to be welded to the wall. It is equally possible, however, for the first and the second mounting devices to be screwed to the wall or for both to be welded to the wall. The first and the second mounting devices advantageously serve in this case for the mounting of a common coupling device.

The first mounting device can be attached for example to the upper wall, i.e., the cover of the clean room. The second mounting device can be attached to the lower wall, i.e. the bottom of the clean room. The coupling device is accordingly supported by one mounting device in each case when entering the clean room and when leaving the clean room.

It is advantageous for one face of the mounting device to be formed at an angle to the horizontal, preferably at an angle of from 5° to 85°, and in a particularly preferred manner at an angle of from 10° to 30°. The face is to be understood as being, in particular, the outer face of the mounting device inside the clean room.

Accordingly, no liquids remain standing on horizontal faces, but liquids always flow off in the direction of the lower wall of the clean room. Liquids are understood to be, inter alia, a condensate or cleaning medium such as foam or sterile water for the removal of the foam.

It is preferable for the mounting device for mounting the coupling device to extend from the wall in the direction of the clean room and, in addition, a support device is provided, which is situated on an external region of this wall.

The support device is likewise suitable for the guidance or the mounting respectively of the coupling device. The support device can be made tubular or angled.

In some embodiments, the support device is adapted to a recess in the wall for the insertion or the replacement respectively of the blow moulding station as a whole.

In some embodiments, a sealing device is provided between the coupling device and the mounting device. The sealing device seals the clean room off from the environment, but at the same time it allows a rotational movement of the coupling device. The seal can thus be a rotary seal, for example a lip seal. Alternatively, a folding bellows which seals the entire mounting device off from the clean room can also be used as the sealing device. In a preferred embodiment the sealing device can also be a hydraulic seal, for example a surge chamber.

It is preferable for the coupling device designed in the form of a main shaft to serve as a pivoting drive for a lateral part of the blow mould and for the second lateral part to be pivoted together with the locking device by way of a coupling mechanism. In this way, it is possible for the two lateral parts to be opened to different degrees although they are pivoted about the main shaft.

The actual drive for the pivoting movement can engage, for example, by cam rollers or even by motors on levers which are arranged on the pivot shaft.

It is preferable for the coupling device to be additionally provided for actuating a lateral part for the actuation of the stressing device, the bottom part and/or a locking device. The locking device can be attached for example to a half of a mould carrier fastened to the blow moulding wheel in an immovable manner, in which case only the second half of the blow mould is arranged so as to be pivotable. Alternatively, the locking device can be attached to the wall of the clean room at a distance from the halves of the mould carrier, so that the coupling device, i.e. the so-called locking shaft, performs for example only a rotational movement about the centre axis thereof. If the locking device has to perform only a rotational movement about the centre axis, then the mounting and sealing of the locking shaft can be carried out in a manner similar to the mounting and sealing of the main shaft.

It is also possible, however, for the locking shaft to perform a movement coupled to the opening of the blow mould at a right angle to the axis of rotation of the main shaft. When in addition a pivoting movement of this type is also provided, the locking shaft is sealed by a folding bellows or other seal which permits a translational as well as a rotational movement.

In contrast to the main shaft, the stressing device and the bottom part in accordance with some embodiments perform a translational movement substantially at a right angle to the face of the upper or lower wall respectively. In addition, in the case of a movement of this type, the mounting of the respective coupling device can be carried out by a mounting device fastened to the wall. In this case, however, care must be taken to ensure that the coupling device does not bring any germs or the like from the environment into the clean room. A contamination of the clean room can be prevented for example by the clean room being at least increased so that the coupling device is situated in a tube-like housing into which germs or the like cannot penetrate. The housing can be closed off in an air-tight manner or can be under permanent over-pressure. Alternatively, the region of the coupling device, which is partially inside and partially outside the clean room, can be acted upon with $H_2O_2$ again when entering the clean room.

In a preferred embodiment the mounting device is at a horizontal distance of at most 10 cm, preferably 5 cm, and in a particularly preferred manner 3 cm, from the blow mould.

It is advantageous for the mounting device to be at least in part at the level of the blow mould in the direction of an axis, which is defined by a shaft which actuates at least one lateral part.

It is particularly advantageous for the mounting device to be brought as closely as possible to the position of the coupling device, at which a force acts upon the coupling device as a result of the pivoting of the lateral parts. The described position on the coupling device is as a rule in the region in which the lateral parts are arranged.

It is preferable for a drive device to be provided in order to move the bottom part, as well as a further drive device in order to move the lateral parts. It is also possible, however, for only one drive device to be provided and for a movement of the lateral parts to be coupled to a movement of the bottom part by way of a coupling device. In this case, it is possible for the coupling device to be arranged at least in part inside the clean room. It is also possible for the coupling device to be arranged completely outside or completely inside the clean room.

It is advantageous for at least one of the drive devices arranged outside the clean room to be coupled to at least one lateral part or to the bottom part by way of a coupling device and for this coupling device to extend through a boundary of the clean room. It is advantageous for the clean room to be bounded by a wall, for example, a flexible or a rigid wall. The wall can also constitute the boundary of the clean room with respect to the non-sterile external region. In particular, a coupling device is to be understood, in some embodiments, as being a device which operates mechanically and which transmits a movement of the drive device to the bottom part or at least one lateral part.

It is advantageous for the sealing device to be a resilient sealing element. In this way, it is possible for the coupling device to be, for example, a rod or a linkage and for a sealing element such as for example a folding bellows to be arranged on this linkage. For the use of a folding bellows of this type, a tight boundary of the clean room can be maintained despite a movement of the coupling device. It is advantageous for at least one portion of the sealing element to follow the coupling device with respect to its movement.

It is advantageous for the drive device to move the bottom part or at least one lateral part along a finite path, i.e. along a movement path which has at least one end point and advantageously two end points, in contrast for example to a movement along a circular or elliptical track.

It is advantageous for a first drive device to be provided for moving the bottom part and a second drive device to be provided for moving the lateral part and for the two drive devices to be arranged outside the clean room.

In another embodiment, the sealing device has a gas lock. In this case, a gas such as water vapour can be introduced into a region to be sealed off and for the water vapour to form a gas barrier.

In addition, a seal can be produced, for example, according to so-called surge chambers. Here, a movable element can be guided in a water container so that a lifting movement is possible without a boundary between a sterile and a non-sterile room being able to be crossed by a gas.

In other embodiments, the apparatus has supply devices for supplying a tempering liquid for the blow moulds and connections for the supply devices are arranged inside the sterile room or clean room, respectively. In addition, a clean room boundary can be provided in such a way that the supply devices for the supply of the tempering liquid and the connections for the supply devices are arranged outside the clean room in the bottom part. It is advantageous for the bottom part and also, in a particularly preferred manner, for the lateral parts to be resistant to cooling water.

In some embodiments, the apparatus can have a sterilization device which is arranged upstream of the actual blow moulding stations and which sterilizes the individual plastics material pre-forms.

In addition, a blow moulding wheel of the blow moulding machine can be reworked, i.e., the region in which a plastics material container is produced from a plastics material pre-form. A region around the actual shaping region of the machine, i.e. the mould carrier with the blow mould, is enclosed in such a way that this region can be sterilized. Here, a sterile room can be defined and for all media and components which cross the boundaries of this sterile room to be designed in such a way that a room sterilized once at the start of production will also remain sterile. On account of the procedure according to the invention it is also possible to prevent grease and ambient air from entering the sterile room.

In the region of the bottom part a lifting movement must be carried out in order to be able to shape a blow moulded container. This lifting movement can be actuated by a cam. Conventional approaches on the other hand require that application of grease. It is therefore advantageous for the aforesaid cam to be arranged outside the clean room. Expressed more precisely, it is possible for the aforesaid cam to extend below the mould carrier, and therefore also below the clean room.

The container can be blow moulded standing on its head, in that the aforesaid cam for the bottom part is situated above the mould carrier and therefore also situated above the clean room.

Other drive devices, such as for example servo motors, hydraulic or pneumatic lifting cylinders or the like would also, however, be possible as the drive device. In addition, linear motors can be used.

The above-mentioned sterile room boundary between the clean room and the environment is set in such a way that a drive device, for example, the cam and the cam roller, remain outside the sterile room. It is advantageous for the clean room to be bounded at the bottom by a boundary which is broken through and advantageously solid.

This breaking through serves, as mentioned above, at least the feed-through of the bottom unit of the blow moulding station, and optionally for the feed-through of the above-mentioned supply and removal means of the tempering media for the bottom mould or the bottom part, respectively.

A folding bellows, which provides a closure of the clean room towards the region of the guide cam, can be positioned between the bottom part and the feed-through.

In addition, the aforesaid folding bellows can be fixed on the feed-through by a suitable clamping apparatus, for example, in the manner of a hose clip. In the event of a change of the product or mould, this side can be releasable.

The folding bellows can project into the interior of the clean room. Also, the folding bellows can extend towards the outside with respect to the clean room.

In some embodiments, the apparatus has a stressing device which acts upon the plastics material pre-forms with a gaseous medium. The stressing device is arranged inside the sterile room and, in addition, a drive device is provided for moving the stressing device.

The stressing device can be, for example, a blow moulding nozzle which, as is known in the prior art, in order to carry out the blow moulding procedure is applied to an aperture of the container or even to a blow mould, in order to act upon the plastics material pre-form, in particular with compressed air. The drive device can move the stressing device to be provided outside the sterile room. A further reduction in the volume of the clean room is possible as a result of this procedure. It is advantageous for a wall, which forms a boundary of the clean room, to move jointly with the individual blow moulding stations.

Certain parts of the conveying device can be arranged in a direction at a right angle to the conveying direction of the containers inside the clean room and for other parts to be arranged outside.

It is preferable for the conveying device to include a conveying wheel which rotates about a pre-set axis, in which case at least the axis or a shaft of the conveying device respectively is situated outside the clean room. This makes it possible for the clean room to be kept as small as possible and thus for the internal volume of the clean room also to be kept small. In addition, it is also possible for as large as possible a number of machine parts—which are not directly in contact with the blow moulding stations—to be able to be guided outside the clean room and also for contamination to be kept low.

It is preferable for the clean room to have at least locally an annular profile or a toroidal profile. The cross-section of this toroidal profile preferably differs from a circular shape. The blow moulding stations are conveyed by the conveying device on a substantially circular path.

In another embodiment, a stretch rod for stretching the plastics material pre-forms is arranged on each blow moulding station. This stretch rod can be arranged completely in the clean room, and preferably inside a housing which is adapted to the stretch rod and which projects out of the annular clean room. Alternatively, the stretch rod can project out of the clean room at least for a time and locally. As is known, the stretch rod is used in order to stretch the plastics material pre-forms.

The clean room can be bounded by a plurality of walls. At least one of these walls to be movable, and in particular rotatable, with respect to another wall.

It is preferable for a wall of the clean room arranged radially on the outside to be arranged so as to be stationary. In this way, a wall with an, in particular, cylindrical external profile can be provided, which bounds the clean room. From the interior of this wall, another wall is provided which bounds the clean room with respect to the other side and which is arranged so as to be rotatable. It is preferable for this wall arranged on the inside to be rotated with the individual blow moulding stations. It is preferable for the aforesaid rotatable wall and the wall arranged so as to be stationary to be situated opposite each other. In addition, the clean room is bounded by a wall in the form of a cover, which can be unitary, or otherwise formed in one piece with the rotatable wall.

At least two walls or one wall and one cover respectively can have a sealing device arranged between them. The sealing device preferably seals off parts movable with respect to one another. In this manner, it is possible, for example, for a wall and a cover to have arranged between them a surge chamber in which is provided a water duct. The water duct can be annular. A portion of the part movable with respect to the water duct is guided. In an embodiment, the apparatus has a supply device in order to transfer the plastics material pre-forms to the conveying device and the supply device is arranged inside the clean room. In this manner, the clean room can have a bulge or a deviation from the otherwise circular cross-section respectively, and the supply device such as for example a conveying star wheel for the pre-forms is arranged accordingly in this bulge. A seamless transfer of the containers from the supply device to the conveying device can take place inside a sterile room.

In another embodiment, the apparatus also has a removal device in order to take on the formed plastics material containers from the conveying device. This removal device is likewise arranged inside the clean room. In this manner, a clean room can also be maintained during the removal of the containers. The unit pre-forms can be introduced arranged upstream into the isolator or the clean room, and the bottles can be removed to a following unit under clean room conditions. The isolator or the clean room can be acted upon with cleaning and sterilization media.

In another embodiment, a sterile gas is provided inside the clean room and this sterile gas is under a pressure which is higher than a pressure outside the clean room. In this manner, the clean room can optionally be kept at a higher pressure level than the environment by the introduction of sterilized air, as a result of which it is possible to prevent the penetration of micro-organisms. In addition, it is possible for an antimicrobial active substance or the like to be supplied continuously to the clean room and for a hygienic environment to be maintained.

A clean room spatially bounded in the blow moulding apparatus permits the conveyance of previously disinfected pre-forms without recontamination both outside and inside to the filling means during the stretch blow moulding procedure. In addition, it is simpler to keep the clean room at a low germ level as compared with the shaping apparatus as a whole.

Other aspects of the present inventive concepts relate to a plant for the production of plastics material containers, which includes an apparatus for the shaping of plastics material containers of the type described herein, as well as a heating device. The heating device can be constructed and arranged on a conveying device of the plastics material pre-forms upstream with respect to the apparatus.

The heating device can be used to heat the pre-forms, so that they can subsequently be expanded in a blow moulding procedure to form containers. A filling device, which fills the containers with a beverage, in particular with a sterilized product, is provided downstream or after the shaping apparatus respectively. In addition, the filling device is arranged in a clean room. Furthermore, the clean room can extend as far as the region of a closing device which closes the containers with a closure.

In addition, the plant can include a sterilization device which sterilizes at least one area of the plastics material pre-forms before reaching the apparatus.

In this case this sterilization can be carried out with a gaseous medium, such as gaseous hydrogen peroxide. It would also be possible, however, for the sterilization to be carried out with the use of radiation, such as for example electron beams and/or UV light. Here, a sterilization device can be provided which, in particular, also sterilizes the internal surface of the plastics material pre-forms. In addition, however, the external surface of the plastics material pre-forms can also be sterilized.

The plant can have another clean room which is arranged upstream of the apparatus in the conveying direction of the plastics material pre-forms. It is preferable for the other clean room to pass into the clean room of the shaping device. In this way, it is possible for the plastics material containers to be conveyed in a continuous manner starting from the sterilization thereof until the closing and nevertheless for the clean rooms required for this to be kept relatively small. In this manner, the clean room can be provided as a duct which extends from the sterilization device as far as the closure device and which in a particularly preferred manner is adapted in each case to the corresponding blow moulding stations or holding devices such as gripping elements for the pre-forms or plastics material containers. The duct can also be interrupted by relatively large spaces. For example, the arrangement of conveying star wheels can be separate, or apart, from their rotary drive and arranged substantially completely in the clean room.

The blow moulding stations have in each case one or more blow moulds, the blow moulds having two lateral parts and one bottom part. The lateral parts and the bottom part jointly form a cavity inside which the plastics material pre-form is shaped into the plastics material container. The regions of the lateral parts bounding the cavity and of the bottom part and preferably all the lateral parts and the bottom part are arranged inside the clean room. The lateral parts or the bottom part can be moved in a drive device which is situated at least in part and preferably completely outside the sterile room.

The expression "blow mould" should be understood to mean not only the two halves of the blow mould, but the entire mould carrier including the respective shells, such as for example the master mould or mould carrier shell. It is usual for a lateral part to comprise at least one mould carrier and one half of a blow mould.

It is preferable for at least one region of the conveying device also to move external to the clean room. In some embodiments, the blow moulding stations are moved on a circular path. In some embodiments, they are moved constantly inside the clean room.

FIG. 1 is a diagrammatic illustration of a conventional plant 50 for producing plastics material containers.

In some embodiments, the plant 50 has a heating device 30 in which plastics material pre-forms 10 are heated. The plastics material pre-forms 10 are guided through the heating device 30 by a conveying device 34, such as a circulating chain, and are heated by a plurality of heating elements 31. The heating device 30 is adjoined by a transfer unit 36 which transfers the pre-forms 10 to a sterilization device 32. The sterilization device 32 likewise has in this case a conveying wheel 37, and sterilization elements can be arranged on the conveying wheel 37 or even so as to be stationary. In this region, sterilization for example by hydrogen peroxide gas or even, as mentioned above, by electromagnetic radiation, is possible. In particular, an internal sterilization of the pre-forms is carried out in this region. In the case of electromagnetic radiation, it is advantageous for radiation fingers to dip into the pre-forms 10 for performing internal sterilization. Furthermore, one or more additional radiators can be provided which sterilize the pre-forms 10 from the outside. When hydrogen peroxide is used, dipping nozzles can be provided for the internal sterilization or alternatively nozzles which in particular, although they do not dip in, move jointly with the pre-forms 10. Additional nozzles can be provided below the pre-form 10 for the external sterilization.

A clean room 6 has an external boundary L. The clean room 6 begins in a region of the sterilization device 32. Sluice devices can be provided in this region in order to introduce the plastics material pre-forms into the clean room 6, and constructed to restrict or prevent the loss of gas from inside the clean room 6.

The sterilization device 32 can be provided upstream of and inside the heating device 30. The heating device 30 can also to be arranged inside the clean room.

The clean room 6 is, as indicated by the broken line L, adapted to the external shape of individual components of the plant 50, for example, a shaping apparatus 1. In this way, the volume of the clean room 6 can be reduced.

The shaping apparatus 1 can include a plurality of blow moulding stations 8 arranged on a conveying wheel 2. The plastics material pre-forms 10 are expanded to form containers 20 at blow moulding stations 8. Although not shown in detail, the entire area of the conveying wheel 2 is situated not inside the clean room 6. Instead, the clean room 6 or isolator respectively is designed to a certain extent in the form of a mini-isolator inside the apparatus as a whole. In this manner, it would be possible for the clean room to be designed to include a duct or the like at least in a region of the shaping apparatus 1.

A supply device 22 transfers pre-forms 10 to the shaping device 1. A removal device 24 removes the finished plastics material containers 20 from the shaping apparatus 1. It will be seen that in the region of the supply device 22 and the removal device 24 that the clean room 6 has recesses in each case which receive the supply and removal devices 22, 24, respectively. A transfer of the plastics material pre-forms 10 to the shaping apparatus 1 or a taking on of the plastics material containers 20 from the shaping apparatus 1 respectively can be carried out in a particularly advantageous manner.

The expanded plastics material containers are transferred by a transfer unit 42 to a filling device 40, and are removed from the filling device 40 by a conveying unit 44. The filling device 40 can also be situated inside the aforesaid clean room 6. In addition, in the case of the filling device it is possible not for the filling device 40 as a whole to be arranged with for example a reservoir for a beverage completely inside the clean room 6, but only those regions in which the containers are actually conveyed. In this respect, the filling device 40 can be similar to the apparatus 1 with respect to the shaping of plastics material pre-forms 10.

In a region of the apparatus 1, the clean room 6 is reduced to as small an area as possible, namely, essentially to the blow moulding stations 8 themselves. On account of this compact design of the clean room 6, it is possible in an easier and more rapid manner to produce a clean room as a whole and, in addition, keeping things sterile in the operating phase is less complicated. In addition, less sterile air is required, which may permit smaller filter units. The risk of uncontrolled swirl formation is also reduced.

The heating device for the heating of the plastics material pre-forms is preferably designed in an aseptic manner. This means that, in a manner different from what is shown FIG. 1, in the region of the heating device 30 the plastics material pre-forms can be conveyed through a clean room. The clean room extends for example continuously by way of the blow moulding machine as far as the filling mechanism. In this case it is possible for the complete heating device 30 to be arranged inside a sterile room, but it is also possible, in particular, for the region in which the plastics material pre-forms are conveyed to be enclosed as a sterile room with respect to the environment in this case as well. In this manner, it is possible for example for the plastics material pre-forms to be conveyed by mandrels or the like, which engage in their aperture and in this case the mandrels project through a wall into a clean room. The clean room can likewise be acted upon with an over-pressure, so that no air from the environment can penetrate the clean room.

The heating device 30 can be in the form of an infrared heating device, as illustrated for example in FIG. 1. A microwave heating device can be used as the heating device. Microwave heating devices of this type for the heating of plastics material pre-forms are known per se from the prior art. A plurality of microwave heating stations can be arranged for example on a carrier wheel.

The plastics material pre-forms can be supplied to these individual heating stations by way of sluices. On account of the design with individual heating stations, a microwave-based heating device is suitable for a combination with sterile rooms.

Figure 2:
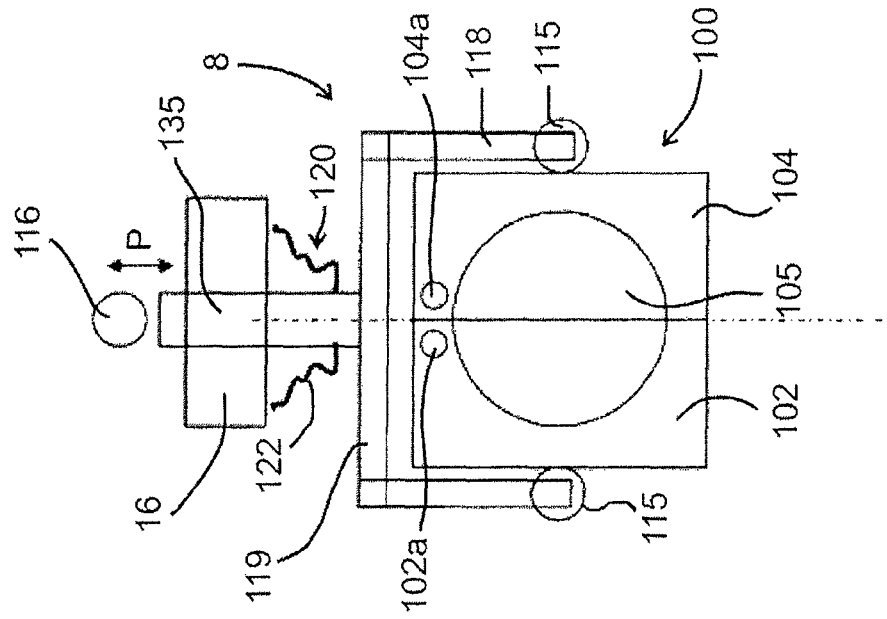
FIG. 2 is a plan view of a conventional clean room in the region of a blow moulding station.

FIG. 2 is a plan view of a conventional clean room in the region of a blow moulding station 8. The blow moulding station 8 has a blow mould 100 (shown greatly simplified and without a carrier) with a first lateral part 102 and a second lateral part 104 which pivot about pivot axes 102a and 104a, respectively. The pivot axes 102a and 104a can attached in a fixed manner relative to the walls 13, 17 or other surface. In their interior, the two lateral parts form a cavity 105 in which plastics material pre-forms can be expanded into plastics material containers. Arms 118 are arranged on the two lateral parts 102 and 104 by way of joints 115 in each case, these arms in turn being provided on a main arm 119. A drive device 116 moves a rod 135 in the direction of a double arrow P, which also moves the arms 118 and 119 in a same or similar direction. The two lateral parts 102 and 104 can be pivoted apart from each other and together respectively about the pivot axes 102a, 104a, respectively, by the movement of the rod 135. In particular, the arms 118 and 119 serve for the locking of the lateral parts 102, 104 to each other.

A sealing device 120 with a folding bellows 122 is arranged on the coupling device 135 on one side and on a boundary wall 16 on the other side. A boundary wall 16 separates the clean room, in which the blow moulding station 8 is arranged, from the non-sterile room, in which the drive device 116 is provided. In this way, a sealing device 120 is provided which screens an opening mechanism, which is associated with the blow mould or the mould carrier respectively, off from the conveying path of the containers or pre-forms.

The folding bellows 122 consists of a material which is selected from a group of materials which can contain but is not limited to plastics materials, ethylene propylene diene monomer (EPDM), India rubber, elastomers, rubber, or steel. The folding bellows 122 can be constructed as a diaphragm bellows or a corrugated bellows or in the form of a combination thereof.

Figure 3:
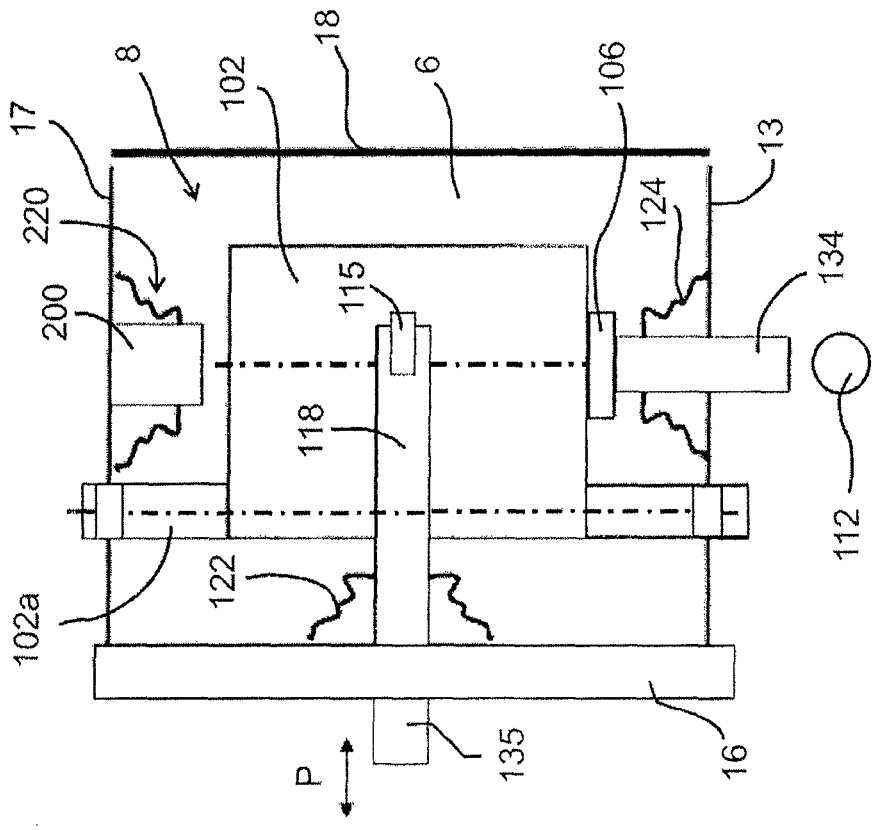
FIG. 3 is a side view of the apparatus shown in FIG. 2.

FIG. 3 is a side view of the apparatus according to the prior art shown in FIG. 2. In the illustration shown in FIG. 3 a drive device 112, which moves a coupling device 134, will be additionally seen, in which case a bottom part 106 which likewise serves for closing off the cavity 105 is arranged in turn on the coupling device 134. A lower wall 13 of the clean room 6 is shown, through which the coupling device 134 can extend. A sealing device 124 such as a folding bellows, seals this movement of the coupling device 134 off with respect to the wall 13.

A wall 18 is situated radially on the outside and which is arranged vertically in this case. The walls 13 and 17 as well as the wall 16 turn jointly with the individual blow moulding stations 8. The clean room 6 can be designed to be relatively close around the blow moulding stations so that a very small volume has to be kept sterile. Altogether, three sealing devices 122, 124, 220 are provided, more precisely, a further sealing device 220 as well, which serves for sealing off the movement of a blow moulding nozzle 200. Another coupling device 135 couples the lateral parts 102, 104 to the drive device 116. A pivot axis 102a is provided for pivoting the lateral part 102, which passes through the walls 13, 17 and is fastened to these walls 13, 17 in an immovable manner.

Figure 4:
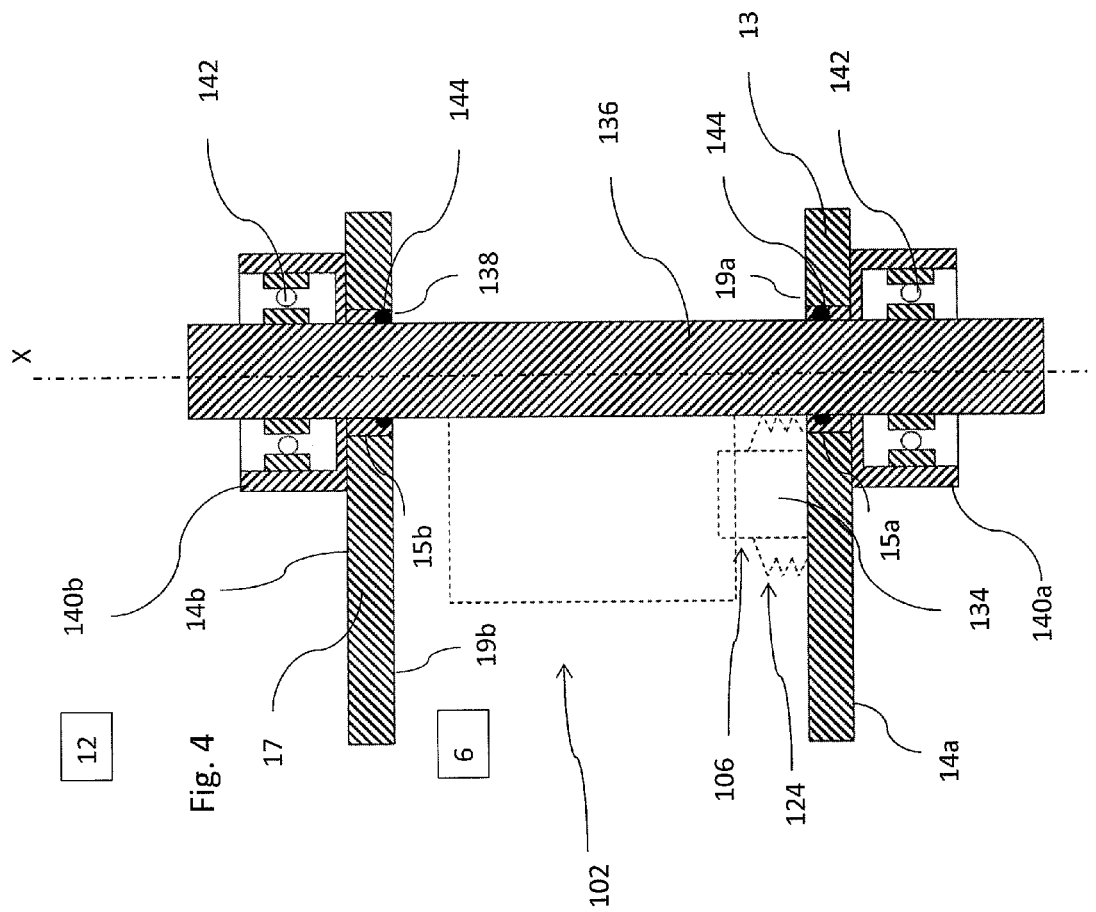
FIG. 4 is a side view of an apparatus according to embodiments of the present inventive concepts.

FIG. 4 is a side view of an apparatus according to embodiments of the present inventive concepts. The apparatus can operate in a plant for example illustrated with respect to FIG. 1 and/or a clean room, for example, illustrated in FIG. 2.

A lateral part 102 of a blow mould and a bottom part 106 are shown. A lateral part, for example, similar to lateral part 104 shown in FIG. 2, is situated behind the lateral part 102 in the plane of the drawing, and is not shown in FIG. 4. The bottom part 106 is attached to a coupling device 134 which is guided through a recess in the wall 13 in order to permit a movement of the bottom part 106 parallel to the axis X which represents the axis of rotation of the coupling device 136. In addition, the axis X is situated substantially at a right angle to the upper and lower walls 13, 17. The movement of the bottom part 106 is necessary in order to close the blow mould 100 completely or to be able the remove the finished blow moulded bottles from the blow mould respectively. The movement of the coupling device 134 without contamination of the clean room 6 is made possible by a folding bellows 124 which bounds the clean room 6 with respect to the environment 12.

In addition, a coupling device 136, or main shaft, is shown in FIG. 4. The main shaft 136 extends through the walls 13 and 17 and is sealed off from the mounting device 140 a, b by a sealing device 144 in the region of the walls 13, 17, which bound or otherwise identify the boundary of the clean room. The mounting device 140a, b and the coupling device 136 are arranged substantially at a right angle to the walls 13, 17.

The sealing device 144 is preferably attached as a boundary to the clean room 6, so that the mounting devices 140 a, b are situated outside the clean room 6. Only the face 138 of the mounting device 140 a, b serves, together with the wall 13, 17, as a boundary of the clean room. The face 138, which constitutes the innermost end of the mounting device 140 a, b, is situated at the highest in the plane of the internal region 19a, b of the wall 13, 17, but does not extend further from there in the direction of the clean room.

Alternatively, the mounting device 140 a, b can be constructed and arranged in an aseptic manner and arranged inside the clean room 6.

The mounting device 140 a, b is directly connected, preferably welded or screwed, to the wall 13 or 17 respectively. The mounting device 140 a, b is thus fastened in an immovable manner to the wall 13, 17 and serves to support the rotatable main shaft 136. It is advantageous for example for the mounting device 140 b to be screwed to the wall 17 and for the second mounting device 140a to be welded to the wall 13. As a result, it is possible not to overdetermine the main shaft 136, but to set the mounting device 140 b on the wall 17 in accordance with predetermined requirements.

In addition, one or more bearing means 142, for example ball bearings, are provided between the mounting device 140 a, b and the main shaft 136, in order to permit a rotational movement of the main shaft 136 about the axis X. These bearings need not be made aseptic, since they are situated outside the clean room.

In FIG. 4, the mounting device 140b is fastened, and preferably screwed, on the external region 14b of the wall 17 and, in addition, on the lateral region 15b, i.e. parallel to the axis X, on the wall 17.

Alternatively, the mounting device 140b can be attached only to the external region 17b of a wall 17. It is preferable, however, for the mounting device 140b to be attached to the wall 17 only in the lateral region 15b which is parallel to the axis X. The mounting device 140a can be fastened to the wall 13 in a similar manner. It is preferable, however, for the mounting device 140a to be welded to the wall 13. The upper wall 17, or the face 19b of the wall 17 respectively, is parallel to the lower wall 13, or the face 19a thereof respectively.

Figure 5:
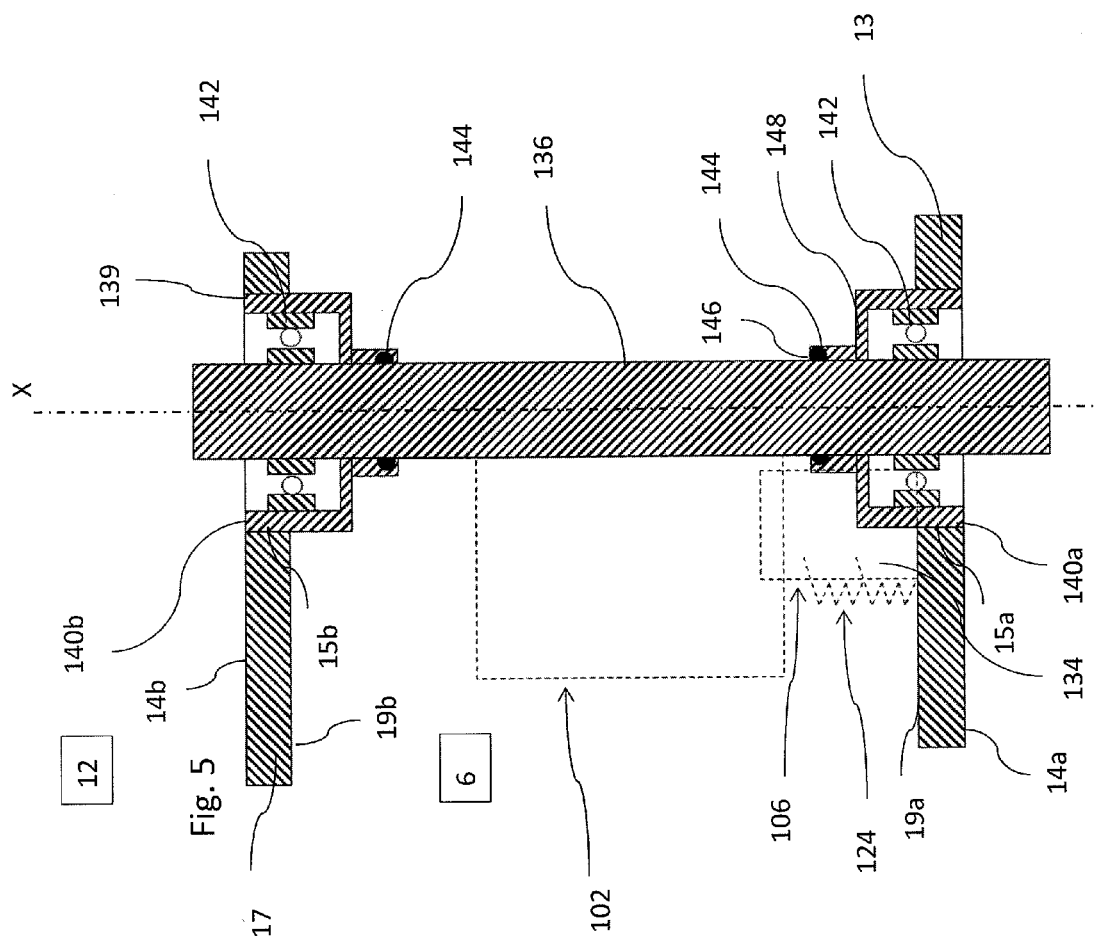
FIG. 5 is a side view of an apparatus according to embodiments of the present inventive concepts.

FIG. 5 is a side view of an apparatus according to embodiments of the present inventive concepts. In a manner similar to FIG. 4, a lateral part 102 of a blow mould 100 and a bottom part 106 are shown. In addition, the walls 13 and 17 are shown which bound the clean room 6 at the top and the bottom. The main shaft 136 passes through the wall 17 at the top and the wall 13 at the bottom. In contrast to FIG. 4, the mounting devices 140 a, b, which, starting from the walls 13 and 17, project into the clean room 6 in each case, are shown in FIG. 5.

The mounting device 140a is fastened, and preferably welded, to the lateral region 15a, which is parallel to the axis X, of the wall 13, in particular, the center axis of the hole which produces the lateral region 15. The inner face, however, may also be involved. One or more bearing means 142, such as for example ball bearings, are attached between the mounting device 140a and the main shaft 136, and a sealing device 144 is attached to the side of the mounting device 140a which adjoins the clean room 6.

The sealing device 144 permits a rotational movement of the main shaft 136 and seals off the clean room 6 from the environment 12.

In a manner similar to the mounting device 140a on the wall 13, an additional mounting device 140b is attached, and preferably screwed, to the wall 17. In FIG. 4, the mounting device 140b is likewise fastened to the lateral region 15b of the wall 17.

Alternatively, one or both of the mounting devices 140a, b can be attached only to the internal region 19a, b of the walls 13, 17. It is preferable for at least one of the two mounting devices 140 a, b to be fastened both to the internal region 19a or 19b and to the lateral region 15a or 15b.

The outermost end of the mounting device 140a, b constitutes the face 139. The outermost possible position of the face 139 is in the plane of the external region 14b. The face 139 can also be situated, however, further towards the inside. The position of this face, which is furthest towards the inside, is in the plane of the internal region 19b.

The face 139 is situated in the direction of the axis X in the region between the plane of the external region 14 a, b and the plane of the internal region 19a, b. In working operation of the apparatus 1, the mounting devices 140a, b are connected to the walls 13 and 17 respectively in an immovable manner. In particular, the walls 17, 13 are situated in a horizontal plane in each case.

In some embodiments, the mounting device 140b is welded to the wall 17 and the mounting device 140a is screwed into the wall 13. In other embodiments, mounting devices 140a, b are both welded or both screwed into walls 13, 17, respectively. The same applies to the embodiment shown in FIG. 4.

In addition, in FIG. 4, the mounting device 140a has two faces 146, 148, each or both preferably formed at an angle relative to the horizontal axis (not shown), and in a particularly preferred manner at an angle of from 5° to 45° to the horizontal, so that liquids, such as for example condensate or liquid or foam cleaning or sterilization agents, can flow off.

The mounting device 140a preferably has only one horizontal face 146 since the mounting device 104a is preferably constructed and arranged in the form of a tube.

Alternatively, the mounting device 140a and/or mounting device 140b can be constructed and arranged in the form of a hexagonal hollow cylinder, or can have a hexagonal external shape and a round internal shape, respectively.

An additional seal (not shown), which holds only the grease or oil—used in the mounting means 142—in the mounting means, can be present between a mounting means, preferably each mounting means, and the sealing device 144.

Figure 6:
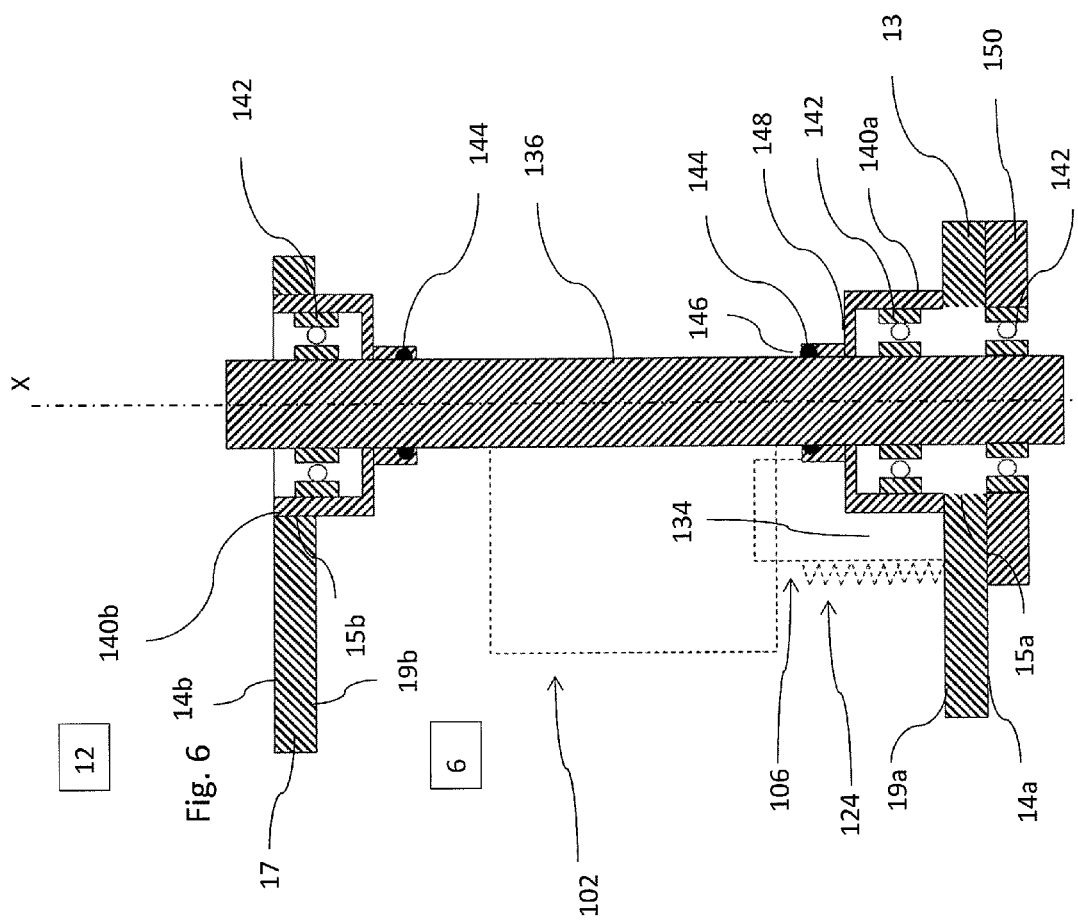
FIG. 6 is a side view of an apparatus according to embodiments of the present inventive concepts.

FIG. 6 is a side view of an apparatus 1 according to embodiments of the present inventive concepts.

The mounting device 140a can be similar to or the same as that described in FIG. 5. In FIG. 5, the mounting device 140a is fastened, and preferably screwed or welded, only to the internal region 19a of the wall 13. Alternatively, it can naturally be attached in a manner similar to FIG. 4.

In FIG. 6, in addition to the mounting device 140a, a support device 150 is used for the mounting or guidance respectively of the main shaft 136. One or more mounting elements 142, for example ball bearings, are also provided in the region of the support device 150. The support device 150 is fastened to the external region 14a of the wall 13. The support device 150 can likewise be in the form of a tube, but it is preferable for it to have a shape, for example angular, which differs therefrom. It is particularly preferred for the support device 150 to be adapted to the recess (not shown) in the wall 13 which is used for the exchange or insertion of the entire blow moulding station 8 from or into the clean room 6. The support device 150 constitutes a separate component.

Combinations of the embodiments shown in FIGS. 4 to 6 are also protected. By way of example one mounting device 140a, b can be attached inside the clean room 6, whereas the other mounting device 140a, b is situated outside the clean room. In addition, the mounting device 140a, b can be provided with the additional support device 150 on one side and only one mounting device 140a, b to be provided outside or inside the clean room 6 on the other side.

In addition, an embodiment of this type is also provided in which the coupling device does not pass through the clean room 6 on both sides, but only on one side, for example only through the wall 13 or only through the wall 17. Here, only one mounting device 140a, b is provided.

The coupling device 134 for the bottom part 106 or the locking shaft (not shown) for example, passes only through the wall 13, whereas the blow moulding nozzle 200 inter alia passes from above, i.e. through the wall 17.

Rotary seals have been shown predominantly as the sealing devices in the figures. The folding bellows can include a gas lock, a vapour lock, a vapour condenser or a liquid lock, for example, a surge chamber. In addition, the sealing device is advantageously temperature-resistant.

All the features disclosed in the application documents are claimed as being essential to the invention, insofar as they are novel either individually or in combination as compared with the prior art.

What is claimed is:

1. An apparatus that forms plastics material containers from pre-forms, the apparatus comprising:
   a conveying device;
   a plurality of blow moulding stations arranged on the conveying device, wherein each of the blow moulding stations includes a blow mould, wherein the blow mould has two lateral parts and a bottom part, wherein the lateral parts and the bottom part jointly form a cavity inside which a plastics material pre-form is shaped into a plastics material container, and wherein at least the areas of the lateral parts bounding the cavity and of the bottom part are inside a clean room inside which the plastics material preforms are conveyed, the apparatus further comprising:
   at least one first drive device that moves the lateral parts or the bottom part of the blow mould, wherein the at least one first drive device is situated at least in part outside the clean room;
   a sealing device that seals the clean room from a region at which the drive device is situated;
   a coupling device that couples the at least one first drive device to at least one lateral part of the two lateral parts, wherein the coupling device extends through at least one wall bounding the clean room; and
   a mounting device that mounts the coupling device, wherein the mounting device is fastened to the wall and extends from the fastening only to one side of the wall, wherein the mounting device comprises two mounting devices for mounting the coupling device, wherein the first mounting device extends from the wall in the direction of the clean room and the second mounting device extends in the direction of the environment.

2. An apparatus according to claim 1, wherein the mounting device has a first portion that abuts the wall and a second portion that is at a right angle to the wall.

3. An apparatus according to claim 1, wherein the mounting device is fixedly and immovably connected to the wall.

4. An apparatus according to claim 1, wherein the first mounting device is screwed to the wall and the second mounting device is welded to the wall.

5. An apparatus according to claim 1, wherein the first and the second mounting devices are constructed and arranged to mount a common coupling device.

6. An apparatus according to claim 1, wherein one face of the mounting device is formed at an angle to a horizontal axis.

7. An apparatus according to claim 6, wherein the angle ranges from 5° to 85°.

8. An apparatus according to claim 6, wherein the angle ranges from 10° to 30°.

9. An apparatus according to claim 1, wherein the mounting device extends from the wall in a direction of the clean room, and wherein the apparatus further comprises a support device at a region external the wall.

10. An apparatus according to claim 9, wherein the support device is adapted to a recess in the wall in order to insert or replace at least one blow moulding station of the blow moulding station.

11. An apparatus according to claim 1, wherein the sealing device is between the coupling device and the mounting device.

12. An apparatus according to claim 1, wherein the coupling device actuates a stressing device, the bottom part of the blow mould, or a locking device.

13. An apparatus according to claim 1, wherein the mounting device is at a horizontal distance of up to 10 cm from the blow mould.

14. An apparatus according to claim 1, wherein the mounting device is at a horizontal distance of up to 3 cm or 5 cm from the blow mould.

15. An apparatus according to claim 1, wherein the mounting device is positioned at least in part at a level of the blow mould in the direction of an x-axis.

16. A plant that produces plastics material containers, comprising:
an apparatus according to claim 1, comprising
a conveying device that conveys pre-forms from which the plastics material containers are produced;
a plurality of blow moulding stations arranged on the conveying device, wherein each of the blow moulding stations includes a blow mould, wherein the blow mould has two lateral parts and a bottom part, wherein the lateral parts and the bottom part jointly form a cavity inside which a plastics material pre-foam is shaped into a plastics material container;
at least one first drive device that moves the lateral parts or the bottom part of the blow mould;
a coupling device that couples the at least one first drive device to at least one lateral part of the two lateral parts; and
a mounting device that mounts the coupling device, wherein the mounting device is fastened to the wall and extends from the fastening only to one side of the wall; and
a heating device arranged on the conveying device of the preforms, the heating device upstream from the apparatus.

17. A plant according to claim 16, further comprising a sterilization device which sterilizes at least one area of the plastics material pre-forms before reaching the apparatus.

18. A plant according to claim 16, further comprising a clean room which is arranged upstream of the apparatus in the conveying direction of the plastics material preforms.

19. An apparatus that forms plastics material containers from pre-forms, the apparatus comprising:
a conveying device;
a plurality of blow moulding stations arranged on the conveying device, wherein each of the blow moulding stations includes a blow mould, wherein the blow mould has two lateral parts and a bottom part, wherein the lateral parts and the bottom part jointly form a cavity inside which a plastics material pre-form is shaped into a plastics material container, and wherein at least the areas of the lateral parts bounding the cavity and of the bottom part are inside a clean room inside which the plastics material preforms are conveyed, the apparatus further comprising:
at least one first drive device that moves the lateral parts or the bottom part of the blow mould, wherein the at least one first drive device is situated at least in part outside the clean room;
a sealing device that seals the clean room from a region at which the drive device is situated;
a coupling device that couples the at least one first drive device to at least one lateral part of the two lateral parts, wherein the coupling device extends through at least one wall bounding the clean room; and
a mounting device that mounts the coupling device, wherein the mounting device is fastened to the wall and extends from the fastening only to one side of the wall, wherein the mounting device extends from the wall in a direction of the clean room, and wherein the apparatus further comprises a support device at a region external the wall.

20. An apparatus that forms plastics material containers from pre-forms, the apparatus comprising:
a conveying device;
a plurality of blow moulding stations arranged on the conveying device, wherein each of the blow moulding stations includes a blow mould, wherein the blow mould has two lateral parts and a bottom part, wherein the lateral parts and the bottom part jointly form a cavity inside which a plastics material pre-form is shaped into a plastics material container, and wherein at least the areas of the lateral parts bounding the cavity and of the bottom part are inside a clean room inside which the plastics material preforms are conveyed, the apparatus further comprising:
at least one first drive device that moves the lateral parts or the bottom part of the blow mould, wherein the at least one first drive device is situated at least in part outside the clean room;
a sealing device that seals the clean room from a region at which the drive device is situated;
a coupling device that couples the at least one first drive device to at least one lateral part of the two lateral parts, wherein the coupling device extends through at least one wall bounding the clean room; and
a mounting device that mounts the coupling device, wherein the mounting device is fastened to the wall and extends from the fastening only to one side of the wall, wherein the mounting device comprises two mounting devices and both mounting devices extend from the wall in a direction of the clean room.

* * * * *